United States Patent
Kim et al.

(10) Patent No.: US 9,781,838 B2
(45) Date of Patent: Oct. 3, 2017

(54) GAS SENSOR AND METHOD OF MANUFACTURING THE SAME

(71) Applicant: Industry-Academic Cooperation Foundation, Yonsei University, Seoul (KR)

(72) Inventors: Hyungjun Kim, Seoul (KR); Kyung Yong Ko, Jeju-do (KR); Jeong-Gyu Song, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 134 days.

(21) Appl. No.: 14/629,437

(22) Filed: Feb. 23, 2015

(65) Prior Publication Data

US 2015/0241386 A1 Aug. 27, 2015

(30) Foreign Application Priority Data

Feb. 24, 2014 (KR) .................. 10-2014-0021444
Jan. 26, 2015 (KR) .................. 10-2015-0012330

(51) Int. Cl.
*G01N 27/00* (2006.01)
*H05K 3/32* (2006.01)
*G01N 27/12* (2006.01)

(52) U.S. Cl.
CPC ............. *H05K 3/32* (2013.01); *G01N 27/125* (2013.01); *G01N 27/127* (2013.01); *Y10T 29/49147* (2015.01)

(58) Field of Classification Search
CPC ...... G01N 27/125; G01N 27/127; H05K 3/32; Y10T 29/49147
See application file for complete search history.

(56) References Cited

U.S. PATENT DOCUMENTS

| 3,791,867 A * | 2/1974 | Broadhead ............ H01M 4/581 429/218.1 |
| 5,429,727 A * | 7/1995 | Vogt .................. G01N 27/4075 204/408 |
| 7,827,852 B2 | 11/2010 | Cui et al. |
| 8,815,160 B2 | 8/2014 | Dolan |

(Continued)

FOREIGN PATENT DOCUMENTS

CN 103718031 4/2014
EP 2533037 12/2012

(Continued)

OTHER PUBLICATIONS

Kim, C. K., et al., A Study on Micro Gas Sensor Utilizing WO3 Thin Films Fabricated by Sputtering Method, The Korea Academia-Industrial Cooperation Society, 4(3), 2003, pp. 139-144.

(Continued)

*Primary Examiner* — Daniel S Larkin
*Assistant Examiner* — Alex Devito
(74) *Attorney, Agent, or Firm* — Procopio, Cory, Hargreaves & Savitch LLP

(57) ABSTRACT

Provided are a gas sensor and a method of manufacturing the same. The gas sensor may include a transition metal chalcogenide layer on a substrate, a metal nano material on the transition metal chalcogenide layer, and an electrode on the transition metal chalcogenide layer with the metal nano material.

13 Claims, 18 Drawing Sheets

(56) References Cited

U.S. PATENT DOCUMENTS

| | | | |
|---|---|---|---|
| 2002/0053522 A1* | 5/2002 | Cumings | C30B 29/605 |
| | | | 205/640 |
| 2003/0199100 A1* | 10/2003 | Wick | G01N 15/065 |
| | | | 436/153 |
| 2003/0235064 A1* | 12/2003 | Batra | B82Y 10/00 |
| | | | 365/100 |
| 2007/0087470 A1* | 4/2007 | Sunkara | C30B 25/00 |
| | | | 438/99 |
| 2014/0065465 A1* | 3/2014 | Johnson | H01M 10/056 |
| | | | 429/158 |
| 2014/0105790 A1 | 4/2014 | Gaudon et al. | |
| 2014/0231933 A1 | 8/2014 | Yu et al. | |

FOREIGN PATENT DOCUMENTS

| | | |
|---|---|---|
| EP | 2718705 | 4/2014 |
| JP | 07-069782 | 3/1995 |
| JP | 2014519042 | 8/2014 |
| KR | 10-2004-0043132 | 5/2004 |
| KR | 10-2012-0100536 | 9/2012 |
| KR | 10-2013-0134828 | 12/2013 |
| KR | 10-2013-0142487 | 12/2013 |
| KR | 10-2014-0037702 | 3/2014 |
| KR | 2014-0074269 | 6/2014 |
| KR | 10-2014-0103015 | 8/2014 |
| KR | 10-2014-0106812 | 9/2014 |
| WO | 2012/168444 | 12/2012 |

OTHER PUBLICATIONS

Song, J-G., et al., Layer-Controlled, Wafer-Scale, and Conformal Synthesis of Tungsten Disulfide Nanosheets Using Atomic Layer Deposition, ACS Nano, 2013, 7(12), pp. 11333-11340.

* cited by examiner

GAS SENSOR AND METHOD OF MANUFACTURING THE SAME

TECHNICAL FIELD

Example embodiments of the inventive concept relate to a gas sensor and a method of manufacturing the same.

BACKGROUND ART

Some of transition metal dichalcogenides (TMDC), such as tungsten disulfide and molybdenum disulfide, exhibit semiconductor characteristics; for example, electric characteristics (e.g., band gap) of them are changed, depending on the number of stacked layers, and thus, they are reported as the next-generation two-dimensional materials.

However, in the case where a transition metal chalcogen layer is formed by the conventional method, there are difficulties in controlling a shape of a layer, changing the number of stacked layers, or forming a layer with a large area. That is, the conventional method has limitation in manufacturing a device, in which a layer with a uniform thickness and a large area is provided.

SUMMARY OF INVENTION

Technical Problem

Example embodiments of the inventive concept provide a gas sensor, in which a transition metal chalcogenide layer with a uniform thickness and a large area is provided, and a method of manufacturing the same.

Example embodiments of the inventive concept provide a gas sensor, which is configured to include a transition metal chalcogenide layer and thereby have high gas adsorption efficiency and high sensitivity, and a method of manufacturing the same.

Solution to Problem

According to example embodiments of the inventive concept, a gas sensor may include a transition metal chalcogenide layer on a substrate, and an electrode on the transition metal chalcogenide layer.

In example embodiments, the gas sensor may further include a metal nano material provided on the transition metal chalcogenide layer to control a band gap of the transition metal chalcogenide layer.

In example embodiments, the metal nano material may include one of Ag, Pt, Au, and Pd.

In example embodiments, the metal nano material may include at least one of metal nano particles, metal nano wires, or metal nano clusters.

In example embodiments, the transition metal chalcogenide may be tungsten disulfide ($WS_2$) and the metal nano material may be a silver (Ag) nano wire.

In example embodiments, the metal nano material may be provided to dope the transition metal chalcogenide layer, thereby reducing the band gap of the transition metal chalcogenide layer.

According to example embodiments of the inventive concept, a method of manufacturing a gas sensor may include forming a transition metal chalcogenide layer on a substrate, and forming an electrode on the transition metal chalcogenide layer.

In example embodiments, the method may further include forming a metal nano material on the transition metal chalcogenide layer.

In example embodiments, the forming of the metal nano material may include applying liquid containing a metal nano material on the transition metal chalcogenide layer, and heating the substrate in an inert gas atmosphere to evaporate the liquid.

In example embodiments, the forming of the transition metal chalcogenide layer may include forming a transition metal oxide layer on the substrate using an atomic layer deposition process, and chalcogenizing the transition metal oxide layer.

In example embodiments, the forming of the transition metal chalcogenide layer may include forming a tungsten oxide layer on the substrate using an atomic layer deposition process, and forming a tungsten disulfide layer, by heat-treating the tungsten oxide layer while supplying sulfide on the tungsten oxide layer.

In example embodiments, the method may further include forming a metal nano material on the transition metal chalcogenide layer.

In example embodiments, the forming of the tungsten disulfide layer may include performing a first thermal treatment at a first temperature, while supplying hydrogen on the substrate, and performing a second thermal treatment at a second temperature higher than the first temperature, while supplying the hydrogen sulfide on the substrate.

In example embodiments, the first thermal treatment may include thermally treating the substrate at a temperature of 300° C. to 500° C. for 30 to 60 minutes, during the supplying of the hydrogen on the substrate, and the second thermal treatment may include thermally treating the substrate at a temperature of 700° C. to 1000° C. for 30 to 60 minutes, during the supplying of the hydrogen sulfide on the substrate.

In example embodiments, the method may further include forming a metal nano material on the transition metal chalcogenide layer.

According to example embodiments of the inventive concept, a method of manufacturing a gas sensor may include forming a transition metal chalcogenide layer on a substrate, forming a band gap control layer on the transition metal chalcogenide layer to control a band gap of the transition metal chalcogenide layer, and forming an electrode on the transition metal chalcogenide layer.

In example embodiments, the forming of the band gap control layer may include forming a metal nano material on the transition metal chalcogenide layer.

In example embodiments, the metal nano material may include at least one of Ag, Pt, Au, or Pd.

According to example embodiments of the inventive concept, a method of forming a transition metal chalcogenide layer may include depositing a transition metal oxide layer on a substrate using an atomic layer deposition process, and chalcogenizing the transition metal oxide layer to synthesize the transition metal chalcogen layer.

In example embodiments, the method may further include forming a metal nano material on the transition metal chalcogenide layer.

Advantageous Effect of Invention

According to example embodiments of the inventive concept, it is possible to manufacture a large-area gas sensor, in which a layer with high thickness uniformity is provided.

According to example embodiments of the inventive concept, it is possible to manufacture a large-area gas sensor having excellent gas adsorption efficiency and high sensitivity to a target gas.

DESCRIPTION OF EMBODIMENTS

Figure 1:
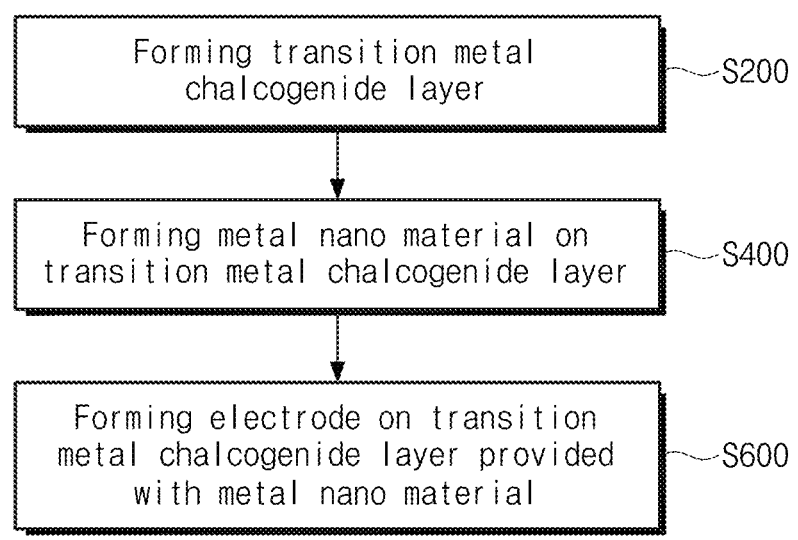
FIG. 1 is a flow chart exemplarily illustrating a method of manufacturing a gas sensor, according to example embodiments of the inventive concept.

Example embodiments of the inventive concepts will now be described more fully with reference to the accompanying drawings, in which example embodiments are shown. Example embodiments of the inventive concepts may, however, be embodied in many different forms and should not be construed as being limited to the embodiments set forth herein; rather, these embodiments are provided so that this disclosure will be thorough and complete, and will fully convey the concept of example embodiments to those of ordinary skill in the art. In the drawings, the thicknesses of layers and regions are exaggerated for clarity. Like reference numerals in the drawings denote like elements, and thus their description will be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments of the inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Example embodiments of the inventive concept relate to a gas sensor, which is configured to have excellent gas adsorption efficiency and thereby to have high sensitivity, and a method of manufacturing such a gas sensor. According to example embodiments of the inventive concept, an atomic layer deposition (ALD) process may be performed to form a transition metal oxide layer with a uniform thickness and a large area, and then, a chalcogenizing treatment may be performed on the transition metal oxide layer to form a transition metal chalcogenide layer with a uniform thickness and a large area. The transition metal chalcogenide layer with a uniform thickness and a large area, which is manufactured by the above method, may be applied to a gas sensing region of a gas sensor, and this makes it possible to realize a gas sensor with high reliability. Further, by forming a metal nano material on the transition metal chalcogenide layer, it is possible to improve stability and sensitivity of a gas sensor.

In the present specification, a metal nano material may refer to a material including a nano material, whose diameter ranges from 0.1 nm to 1000 nm. The metal nano material may be provided in the form of a nano particle, a nano wire, or a nano cluster, and the nano wire may be provided in the form of a circular pillar, whose sectional diameter ranges from 0.1 nm to 1000 nm.

Hereinafter, example embodiments of the inventive concept will be described in more detail with reference to the accompanying drawings.

FIG. 1 is a flow chart exemplarily illustrating a method of manufacturing a gas sensor, according to example embodiments of the inventive concept.

According to example embodiments of the inventive concept, as shown in FIG. 1, a method 100 of manufacturing a gas sensor may include forming a transition metal chalcogenide layer (in S200), forming a metal nano material on the transition metal chalcogenide layer (in S400), and forming an electrode on the transition metal chalcogenide layer (in S600).

In other example embodiments, the step S400 of forming the metal nano material on the transition metal chalcogenide layer may be omitted.

Further, the method of manufacturing a gas sensor according to example embodiments of the inventive concept does not need to be limited to the specific order of forming a metal nano material on the transition metal chalcogenide layer and then forming the electrode, as shown in FIG. 1. In other words, according to other example embodiments of the inventive concept, the method of manufacturing a gas sensor may be performed in such a way that an electrode is formed on a transition metal chalcogenide layer and then a metal nano material is formed, and as an example, the metal nano material may be selectively formed on a gas sensing region, where the electrode is not formed.

Hereinafter, the step S200 of forming the transition metal chalcogenide layer will be described in detail with reference to FIGS. 2 and 3.

Figure 2:
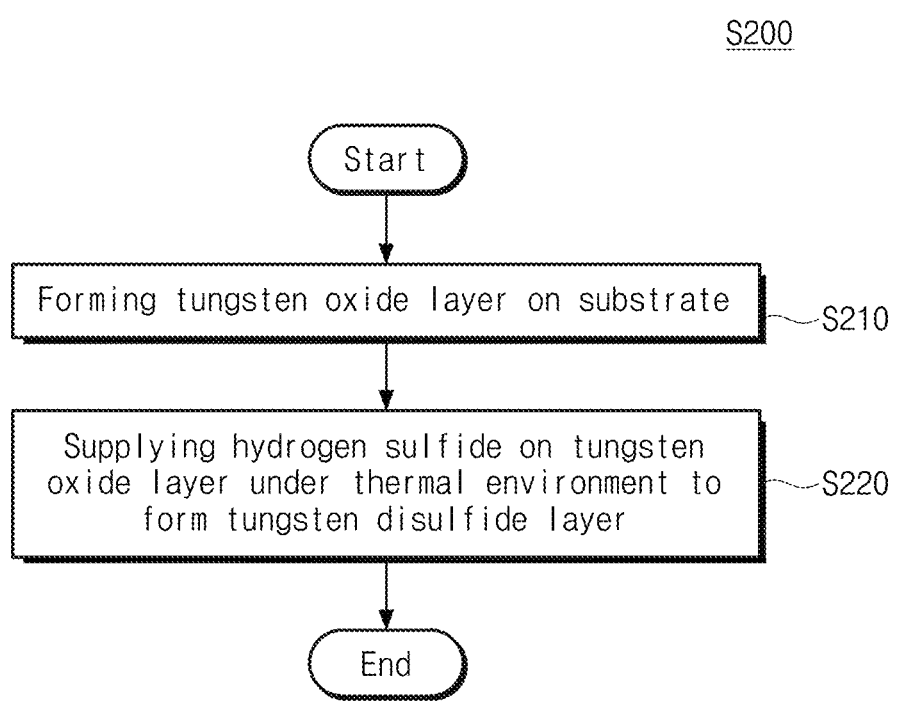
FIG. 2 is a flow chart illustrating a method of forming a tungsten disulfide layer, which is presented as an example of a step S200 for forming a transition metal chalcogenide layer.

FIG. 2 is a flow chart illustrating a method of forming a tungsten disulfide layer, which is presented as an example of the step S200 for forming the transition metal chalcogenide layer.

As shown in FIG. 2, the formation of the tungsten disulfide layer may include a step S210 of forming a tungsten oxide layer on a substrate and a step S220 of supplying hydrogen sulfide on the tungsten oxide layer under the thermal environment to form a tungsten disulfide layer.

In example embodiments, the step S210 of forming the tungsten oxide layer may be performed by an atomic layer deposition (ALD) process including steps of supplying a tungsten precursor into a deposition chamber provided with the substrate, supplying a purge gas to purge the deposition chamber, supplying oxygen source gas into the deposition chamber, and supplying a purge gas to purge the deposition chamber. Further, the steps of supplying the tungsten precursor onto the substrate, supplying the purge gas to purge the deposition chamber, supplying the oxygen source gas onto the substrate, and supplying the purge gas to purge the deposition chamber may be repeated a predetermined number of times.

In example embodiments, the step of supplying the tungsten precursor onto the substrate may include using inert gas as carrier gas to supply tungsten precursor gas onto the substrate. As an example, $WH_2(iPrCp)_2$ or $W(CO)_6$ may be used as the tungsten precursor gas, but example embodiments of the inventive concepts may not be limited thereto.

The tungsten precursor gas may be delivered by the inert gas at a temperature of 25-100° C. Argon gas may be used as the inert gas, but example embodiments of the inventive concepts may not be limited thereto.

After supplying the tungsten precursor gas onto the substrate, the chamber provided the substrate may be purged with the inert gas.

Thereafter, the oxygen source gas may be supplied onto the substrate and may be reacted with the tungsten precursor gas adsorbed on the substrate, thereby forming the tungsten oxide layer. The oxygen source gas to be supplied onto the substrate may be provided using water, ozone, oxygen plasma, or any combination thereof, but example embodiments of the inventive concepts may not be limited thereto.

The oxygen may be supplied on the substrate, on which the tungsten precursor is adsorbed, to synthesize the tungsten oxide layer, and then, the chamber provided the substrate may be purged with the inert gas.

In exemplary embodiments, the supplying of the tungsten precursor gas (A), the purging (B), the supplying of the oxygen (C), and the purging (D) may be performed to meet a ratio in process duration time, which is given by A:B:C:D=3 to 5:5 to 12:3 to 5:5 to 12. For example, the supplying of the tungsten precursor gas (A) may be performed for 5 seconds, the purging (B) may be performed for 12 seconds, the supplying of the oxygen (C) may be performed for 5 seconds, and the purging (D) may be performed for 12 seconds.

Figure 3:
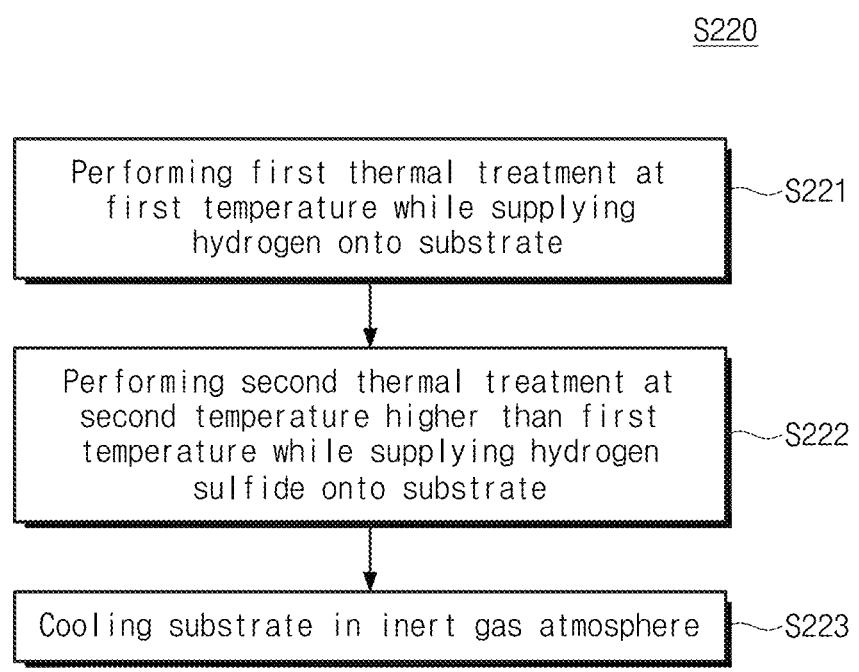
FIG. 3 is a flow chart illustrating an example of a step S220 for forming a tungsten disulfide layer according to example embodiments of the inventive concept.

FIG. 3 is a flow chart illustrating an example of the step S220, in which hydrogen sulfide is supplied onto the tungsten oxide layer under the thermal environment, to form a tungsten disulfide layer according to example embodiments of the inventive concept.

As shown in FIG. 3, the step S220 of forming the tungsten disulfide layer may include a step S221 of performing a first thermal treatment at a first temperature while supplying hydrogen onto the substrate, a step S222 of performing a second thermal treatment at a second temperature higher than the first temperature while supplying hydrogen sulfide onto the substrate, and a step S223 of cooling down the substrate in an inert gas atmosphere.

In other words, the step S220 of forming the tungsten disulfide layer may be performed through two thermal treatment steps.

The step S221 of performing the first thermal treatment at the first temperature while supplying hydrogen onto the substrate may be a process for removing contaminants (e.g., organic materials) from a surface of the tungsten oxide layer.

The step S222 of performing the second thermal treatment at the second temperature while supplying hydrogen sulfide onto the substrate may be a sulfuration process for transforming the tungsten oxide layer to the tungsten disulfide layer.

In exemplary embodiments, the first thermal treatment S221 may include a step of thermally treating the substrate, on which the hydrogen is being supplied, at a temperature of 300 to 500° C. of 30 to 60 min. In the first thermal treatment S221, the hydrogen gas may be supplied at a flow rate of 10 to 30 sccm, and the inert gas may be supplied at a flow rate of 10 to 30 sccm.

The second thermal treatment S222 may include a step of thermally treating the substrate, on which the hydrogen sulfide is being supplied, at a temperature of 700 to 1000° C. of 30 to 60 min. In the second thermal treatment S222, the hydrogen sulfide gas may be supplied at a flow rate of 5 to 30 sccm, and the inert gas may be supplied at a flow rate of 30 to 50 sccm.

As described above, by using an ALD process, it is possible to uniformly form the tungsten oxide layer on a large area, and by performing the sulfuration process, the tungsten disulfide layer can be formed to have a uniform thickness and a large area.

The step S400 of forming the metal nano material on the transition metal chalcogenide layer will be described in detail below.

In the step S400 of forming the metal nano material, the metal nano material may be formed by a vacuum process, such as atomic layer deposition (ALD), chemical vapor deposition (CVD), and physical vapor deposition (PVD) processes, or a liquid process, such as spin coating and inkjet printing processes, but example embodiments of the inventive concepts may not be limited thereto.

In the case where a spin coating process is used to form the metal nano material, liquid containing a metal nano material may be coated on the transition metal chalcogenide layer, be rotated at a high speed, and then the substrate may be heated in an inert gas atmosphere to evaporate the liquid, and thus, the metal nano material may be uniformly formed on the transition metal chalcogenide layer. As an example, the liquid may be liquid with volatility.

As described above, since a metal nano material is formed on a transition metal chalcogenide, a gas sensor can be manufactured to have higher gas sensitivity.

The step S600 of forming an electrode on the transition metal chalcogenide layer will be described in more detail below.

In example embodiments, the step S600 of forming an electrode on the transition metal chalcogenide layer may include depositing a gold layer on a portion of the transition metal chalcogenide layer using a shadow mask and depositing a chromium layer on the gold layer to form an electrode. One of metals other than gold and chromium may also be used for the electrode, and a single kind of metal may be used for the electrode.

Up to now, a method of manufacturing a gas sensor according to example embodiments of the inventive concept has been described. Hereinafter, a structure of the gas sensor manufactured by the method will be described with reference to FIG. 4.

Figure 4:
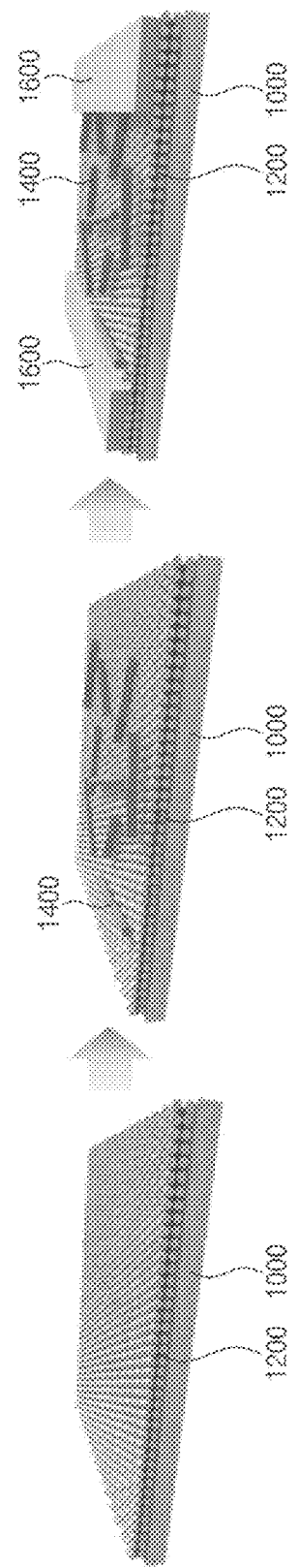
FIG. 4 is a schematic diagram illustrating a structure of a gas sensor according to example embodiments of the inventive concept.

FIG. 4 is a schematic diagram illustrating a structure of a gas sensor according to example embodiments of the inventive concept. As shown in FIG. 4, a gas sensor according to example embodiments of the inventive concept may include a transition metal chalcogenide layer 1200 on a substrate 1000, a metal nano material 1400 on the transition metal chalcogenide layer 1200, and an electrode 1600 on the transition metal chalcogenide layer 1200. Similar to that shown in FIG. 1, to provide understanding for a gas sensor according to example embodiments of the inventive concept, FIG. 4 illustrates a gas sensor provided with a metal nano material, but according to other example embodiments of the inventive concept, a gas sensor may be configured not to include such a metal nano material.

The substrate 1000 may include a silicon (Si) substrate and a silicon dioxide ($SiO_2$) layer formed on the silicon substrate, but example embodiments of the inventive concepts may not be limited thereto.

The transition metal chalcogenide layer 1200 may include at least one of $WS_2$, $MoS_2$, $MoSe_2$, or $WSe_2$. In other words, the transition metal chalcogenide layer 1200 may be formed of or include $WS_2$, $MoS_2$, $MoSe_2$, $WSe_2$, and any combination thereof.

As described with reference to FIGS. 2 through 3, the transition metal chalcogenide layer 1200 may be formed by performing an atomic layer deposition process to form a transition metal oxide layer with a uniform thickness and a large area and then performing a chalcogenizing process on the transition metal oxide layer to form the transition metal chalcogenide layer 1200 with a uniform thickness and a large area. The layer number of the transition metal chalcogenide layer 1200 may be controlled by adjusting the cycling number of ALD processes for forming the transition metal oxide layer.

The metal nano material 1400 may be formed to have a structure consisting of metal nano particles, metal nano wires, or metal nano clusters. In other words, the metal nano material 1200 may be formed to include particles, wires, clusters, and any combination thereof, which are provided on the transition metal chalcogenide.

The metal for the metal nano material may include at least one of Ag, Pt, Au, or Pd. Since Ag, Pt, Au, and Pd are precious metals having stability higher than other metals and exhibit a catalytic effect, the use of the metal nano material makes it possible to increase an adsorption ratio of targeted gas molecules.

According to example embodiments of the inventive concept, in the case where the transition metal chalcogenide layer 1200 is a tungsten disulfide ($WS_2$) layer, the metal nano material may be a silver (Ag) nano wire. In the case where the silver nano material is formed on the tungsten disulfide layer, the tungsten disulfide layer exhibiting p-type semiconductor characteristics may be doped to exhibit electric characteristics similar to those of an intrinsic semiconductor, and this makes it possible to improve sensitivity of a gas sensor. This will be described with reference to FIGS. 12 through 15.

The electrode 1600 may be locally formed on a region of the transition metal chalcogenide layer 1200. In example embodiments, two electrodes may be formed on a region of the transition metal chalcogenide layer 1200. In certain embodiments, the electrode 1200 may include a gold layer and a chromium layer on the gold layer, but in certain embodiments, the electrode 1200 may be formed of or include other metals or a single kind of metal.

Methods of manufacturing a gas sensor according to first to sixth embodiments of the inventive concept will be described in more detail below.

First Embodiment—A Single Layer of $WS_2$

First, an atomic layer deposition process was performed to form a tungsten oxide layer on a silicon dioxide ($SiO_2$) layer provided on a silicon substrate. To form the tungsten oxide layer on the silicon dioxide ($SiO_2$) layer, $WH_2(iPrCp)_2$ was used as a tungsten precursor and oxygen was used as a reactant.

In detail, argon gas was injected into a canister containing $WH_2(iPrCp)_2$ at a flow rate of 50 sccm, while heating the canister to a temperature of 95° C. Thereafter, the silicon substrate with the silicon dioxide ($SiO_2$) layer was exposed to the tungsten precursor for 5 seconds, and a chamber loaded with the silicon substrate was purged with argon gas for 12 seconds.

Thereafter, oxygen gas was supplied into the chamber at a flow rate of 300 sccm, and, in the chamber, plasma of 200 W was generated to react the tungsten precursor adsorbed on the silicon dioxide (SiO$_2$) layer with the oxygen, during the supply of the oxygen gas. As a result, a tungsten oxide layer was synthesized. The oxygen gas was supplied for 5 seconds, and thereafter, the chamber was purged with argon gas for 12 seconds.

During the formation of the tungsten oxide layer, the chamber was maintained at a temperature of 300° C.

A single layer of tungsten oxide, 1 L, was formed by 20 cycles, each consisting of the afore described steps of supplying the tungsten precursor, purging the chamber, supplying the oxygen, and purging the chamber.

Thereafter, a thermal treatment was performed when hydrogen sulfide was supplied onto the tungsten oxide layer, and thereby a tungsten disulfide layer was formed.

In detail, the sample was moved to a chamber with a tube furnace and was heated from the room temperature to a temperature of 470° C. for 10 minutes, while supplying hydrogen and argon gases into the chamber at flow rates of 25 sccm and 25 sccm, respectively.

Next, the sample was thermally treated at the temperature of 470° C. of 1 hour, while supplying the hydrogen and argon gases into the chamber at flow rates of 25 sccm and 25 sccm, respectively.

Next, the sample was heated from 470° C. to 1000° C. for 1 hour 30 minutes, while supplying hydrogen sulfide gas and argon gas into the chamber at flow rates of 5 sccm and 50 sccm, respectively.

Afterwards, the sample was thermally treated at the temperature of 1000° C. for 30 minutes, while supplying hydrogen sulfide gas and argon gas into the chamber at flow rates of 5 sccm and 50 sccm, respectively.

Next, the sample was cooled down to the room temperature in an argon atmosphere, and as a result, the single tungsten disulfide layer, 1 L, was formed.

Thereafter, a gold (Au) layer was deposited on a region of the tungsten disulfide layer using a shadow mask, and a chromium (Cr) layer was deposited on the gold layer to form the electrode.

Second Embodiment—Two Layers of WS$_2$

A gas sensor with two tungsten disulfide layers was formed by a process, which was performed in substantially the same manner as that of the first embodiment, but in which the tungsten oxide layer thereof was formed by 30 cycles, each consisting of steps of supplying a tungsten precursor, purging a chamber, supplying oxygen, and purging the chamber.

Third Embodiment—Four Layers of WS$_2$

A gas sensor with four tungsten disulfide layers was formed by a process, which was performed in substantially the same manner as that of the first embodiment, but in which the tungsten oxide layer thereof was formed by 50 cycles, each consisting of steps of supplying a tungsten precursor, purging a chamber, supplying oxygen, and purging the chamber.

Fourth Embodiment—A Layer of WS$_2$/Nano Wires of Ag

The same process as that of the first embodiment was performed, but silver nano wires were formed after the formation of the tungsten disulfide layer.

In detail, silver nano wires were synthesized, and then, silver nano wires of 0.29 wt % were dipped in ethanol to form ethanol solution provided with the silver nano wires.

Next, the tungsten disulfide layer was loaded in a spin coater, one or two drops of the ethanol solution with the silver nano wires was dropped on the tungsten disulfide layer, and then, a spin coating process was performed on the resulting structure at a speed of 1000 rpm for 15 seconds.

Afterwards, the tungsten disulfide layer was thermally treated at a temperature of 90° C. for 20 minutes in a nitrogen gas atmosphere to evaporate the ethanol and thereby form the silver nano wires on the tungsten disulfide layer.

Thereafter, an electrode was formed by the same method as that of the first embodiment.

Fifth Embodiment—Two Layers of WS$_2$/Nano Wires of Ag

A gas sensor with two tungsten disulfide layers was formed by a process, which was performed in substantially the same manner as that of the fourth embodiment, but in which the tungsten oxide layer thereof was formed by 30 cycles, each consisting of steps of supplying a tungsten precursor, purging a chamber, supplying oxygen, and purging the chamber.

Sixth Embodiment—Four Layers of WS$_2$/Nano Wires of Ag

A gas sensor with four tungsten disulfide layers was formed by a process, which was performed in substantially the same manner as that of the fourth embodiment, but in which the tungsten oxide layer thereof was formed by 50 cycles, each consisting of steps of supplying a tungsten precursor, purging a chamber, supplying oxygen, and purging the chamber.

The following is the description of performance of gas sensors, which were manufactured by the methods according to the above embodiments.

Figure 5:
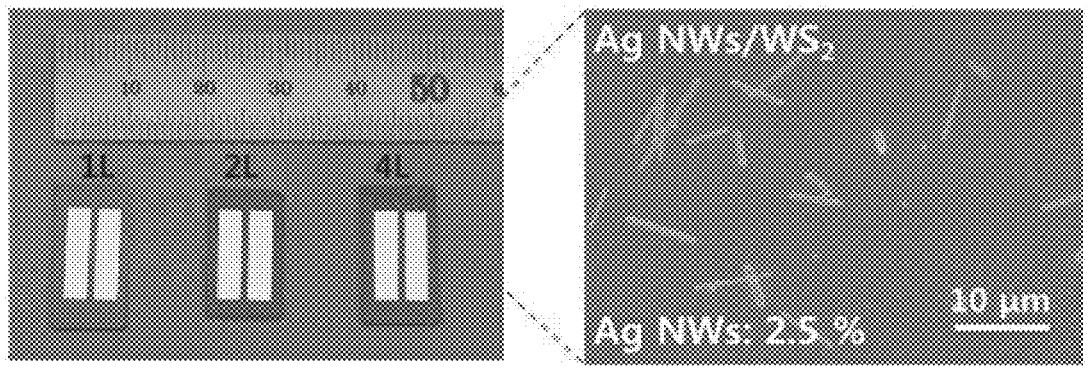
FIG. 5 is an image showing gas sensors and parts thereof, according to fourth, fifth, and sixth example embodiments of the inventive concept.

FIG. 5 is an image showing gas sensors and parts thereof, according to fourth, fifth, and sixth example embodiments of the inventive concept.

In detail, the left image of FIG. 5 show gas sensors, which were manufactured according to the methods of the fourth, fifth, and sixth embodiments and thereby had one, two, and four tungsten disulfide layers denoted by reference numerals of 1 L, 2 L, and 4 L. The right image of FIG. 5 is a microscope image of a portion of the gas sensor with four tungsten disulfide layers (that is, according to the sixth embodiments). As shown in the right image of FIG. 5, nano wires were uniformly formed on a tungsten disulfide layer (that is, to have an area ratio of 2.5% with respect to the total area of the tungsten disulfide layer).

FIGS. 6A, 6B, 7A, and 7B are graphs showing temporal changes in current of gas sensors according to example embodiments of the inventive concept, when they are exposed to nitrogen dioxide gas. In detail, the graphs of FIGS. 6A, 6B, 7A, and 7B show temporal changes in current of the gas sensors according to second, fifth, third, and sixth example embodiments, respectively, of the inventive concept, when they are exposed to nitrogen dioxide gas.

First, FIGS. 6A and 6B and FIGS. 7A and 7B show that all of the gas sensors according to the example embodiments of the inventive concept were responsive to the target gas (i.e., the nitrogen dioxide gas) and current thereof were changed. Further, when the nitrogen dioxide gas was removed, a current passing through each gas sensor was restored to a value similar to that before the supplying of the nitrogen dioxide gas, and this shows that the gas sensor can be repeatedly used.

Also, FIGS. 6A and 6B and FIGS. 7A and 7B show a change in current of the gas sensor caused by the presence or absence of the silver nano wires, when other conditions are the same. By comparing FIG. 6A with FIG. 6B, one can see that the gas sensor with silver nano wires (i.e., of FIG. 6B) had a more stable signal property (for example, much better characteristics in terms of a reaction speed in a gas injection stage and a current restoring speed in an air injection stage), compared with that of FIG. 6A. By comparing FIG. 7A with FIG. 7B, one can see that there was no significant difference in signal stability, but the gas sensor with silver nano wires (i.e., of FIG. 7B) had a much fast current-restoring speed, at an air supplying stage, compared with that of FIG. 7A.

Figure 6A:
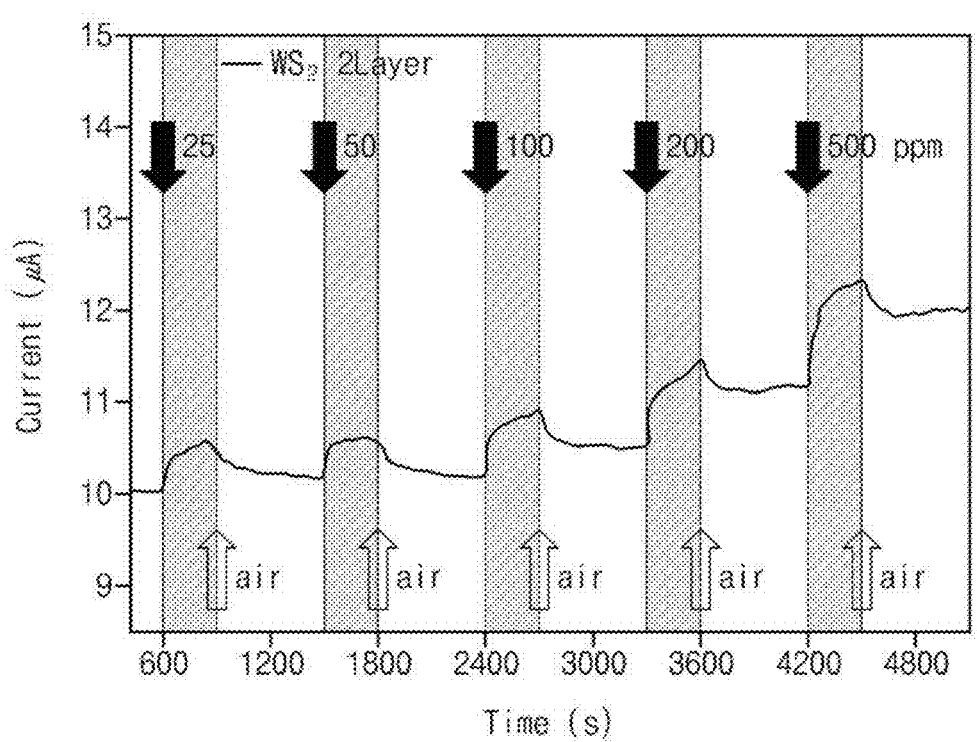
FIGS. 6A, 6B, 7A, and 7B are graphs showing temporal changes in current of gas sensors according to example embodiments of the inventive concept, when they are exposed to nitrogen dioxide gas.
Figure 6B:
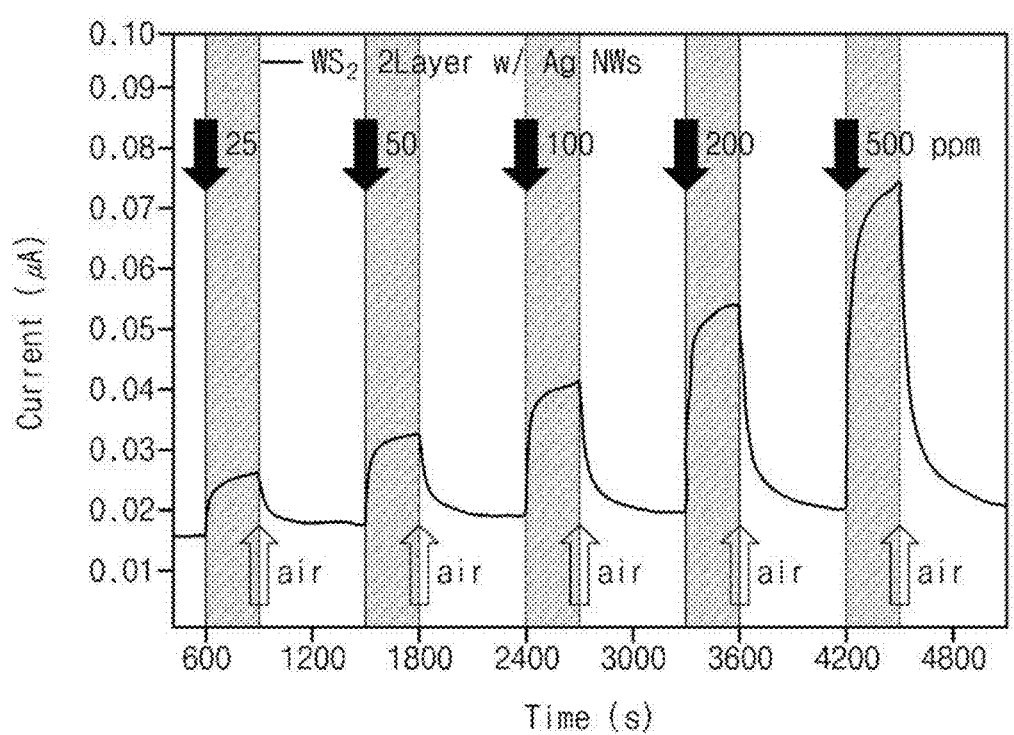
Figure 7A:
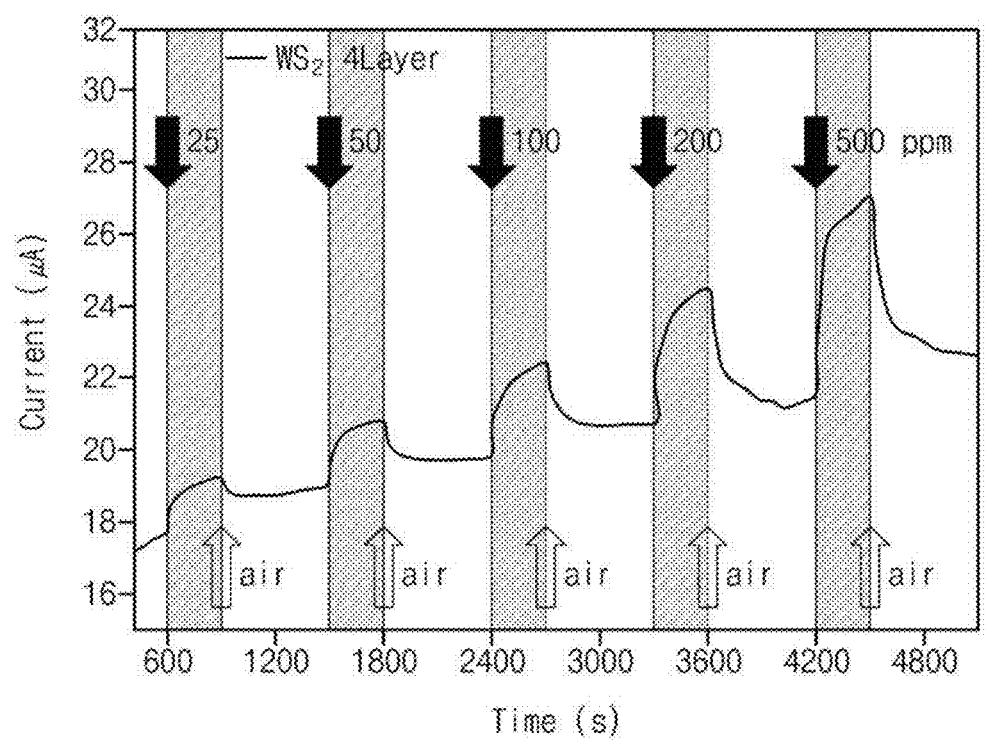
Figure 7B:
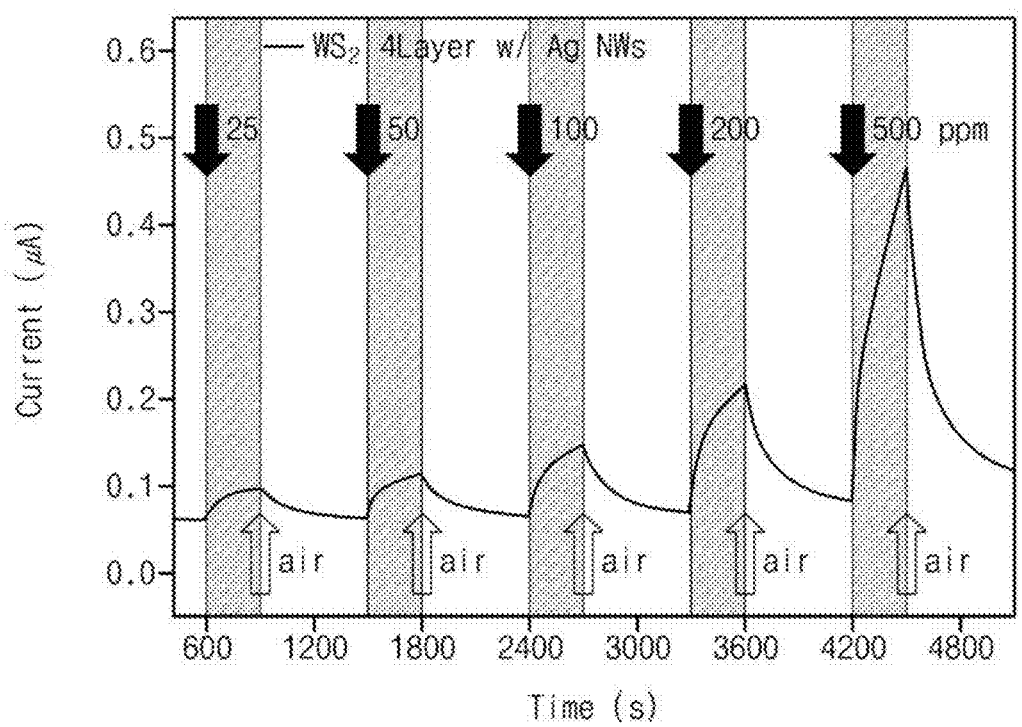
Figure 8A:
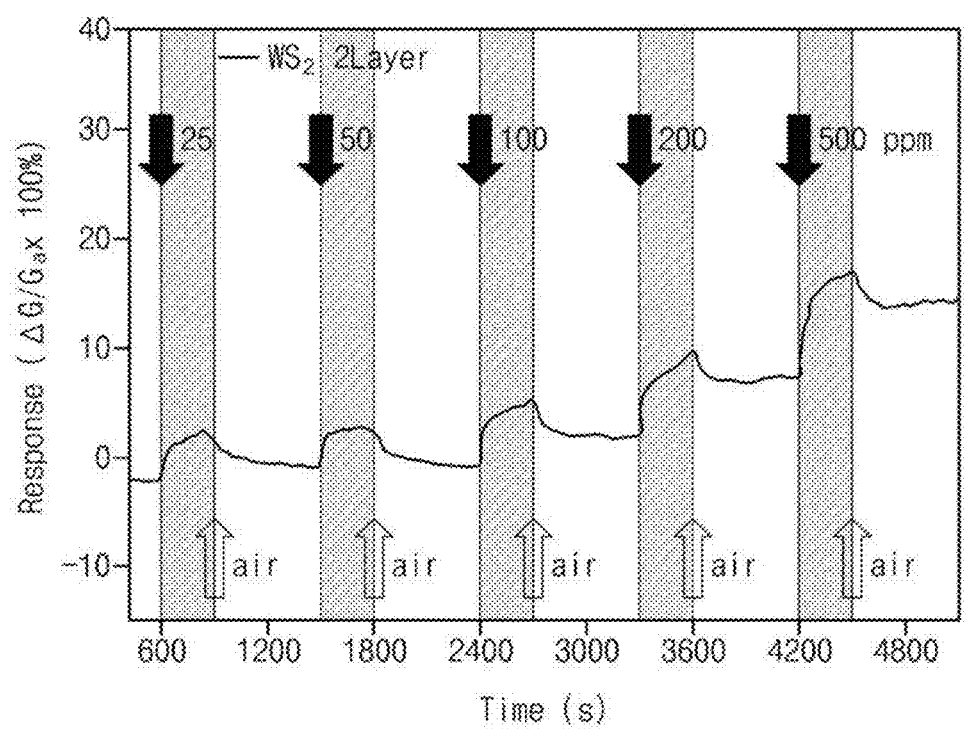
FIGS. 8A, 8B, 9A, and 9B are graphs showing sensitivities to nitrogen dioxide gas of gas sensors according to example embodiments of the inventive concept.
Figure 8B:
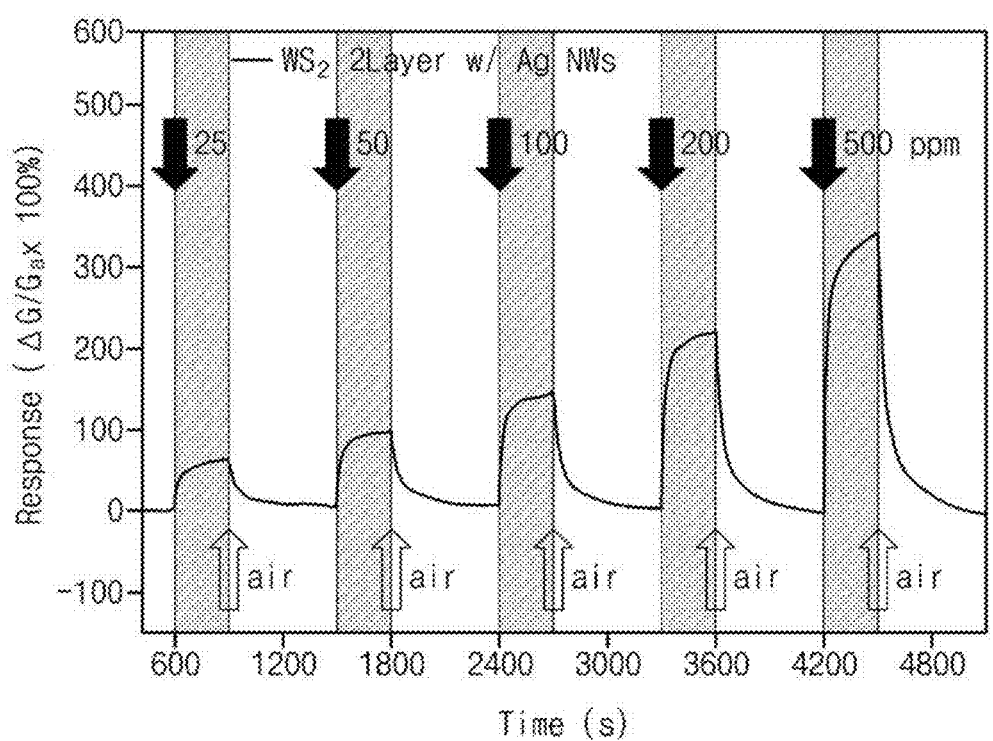
Figure 9A:
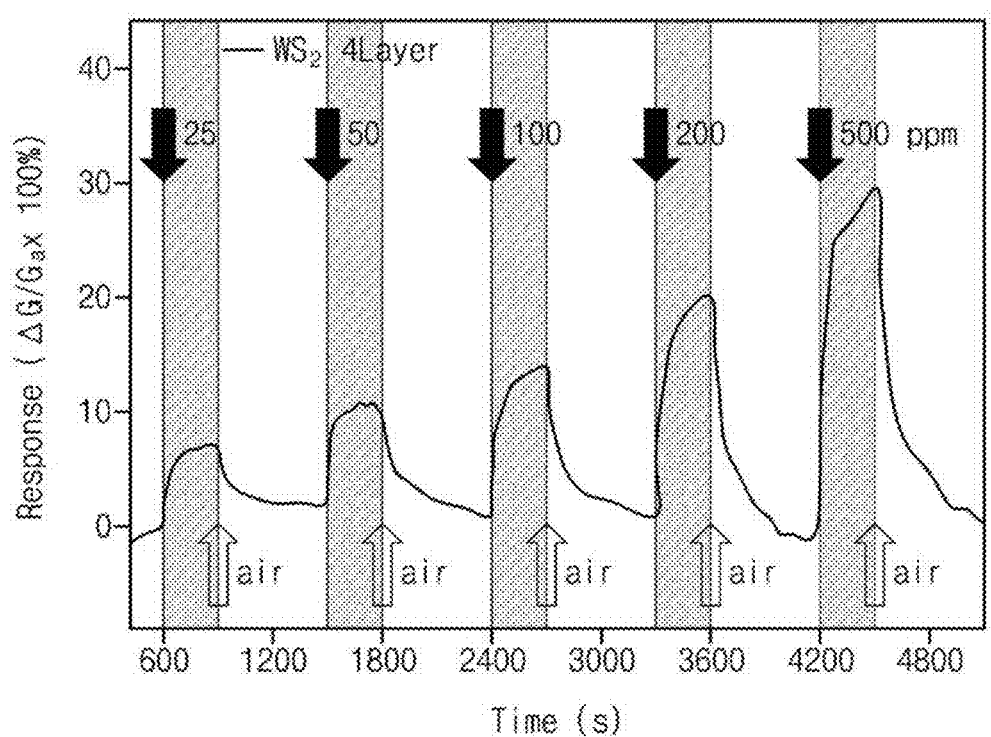
Figure 9B:
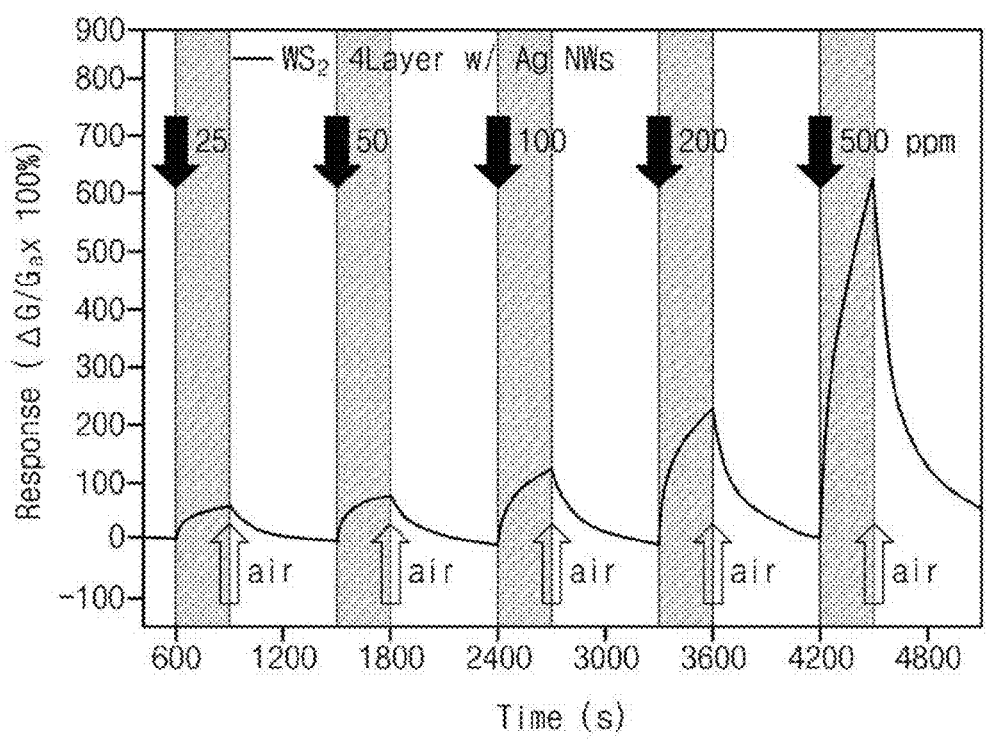

Referring to FIGS. 6A and 7A, a change in current passing through the gas sensor was higher in the case of four tungsten disulfide layers (i.e., of FIG. 7A) than in the case of two tungsten disulfide layers (i.e., of FIG. 6A).

FIGS. 8A, 8B, 9A, and 9B are graphs showing sensitivities to nitrogen dioxide gas of gas sensors according to example embodiments of the inventive concept. In detail, the graphs of FIGS. 8A, 8B, 9A, and 9B show sensitivities to nitrogen dioxide gas of the gas sensors according to the second, fifth, third, and sixth example embodiments, respectively, of the inventive concept.

FIGS. 8A, 8B, 9A, and 9B show a change in sensitivity of the gas sensor caused by the presence or absence of the silver nano wires, when other conditions are the same. In other words, by comparing FIG. 8A with FIG. 8B, one can see that the gas sensor provided with the silver nano wires (i.e., of FIG. 8B) had much better sensitivity than that of FIG. 8A. Further, by comparing FIG. 9A with FIG. 9B, one can see that, similar to the above result of FIGS. 8A and 8B, the gas sensor with the silver nano wires had much better sensitivity.

Figure 10:
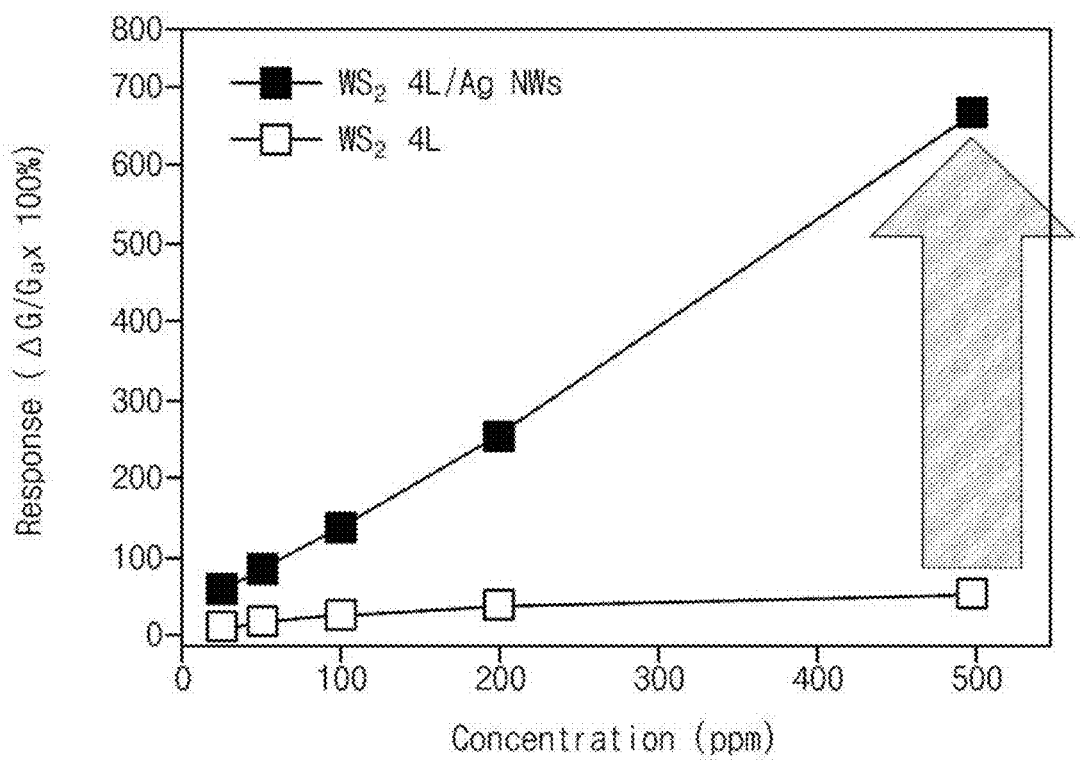
FIG. 10 is a graph comparatively showing sensitivities of gas sensors according to third and sixth example embodiments of the inventive concept.

FIG. 10 is a graph comparatively showing sensitivities of gas sensors according to third and sixth example embodiments of the inventive concept.

As illustrated in FIG. 10, one can see that the gas sensor with silver nano wires (e.g., of the sixth embodiment) had a significantly higher sensitivity than that of the third embodiment. That is, the gas sensor of the sixth embodiment had sensitivity higher by about 12 times, compared with that of the third embodiment, when the gas sensors were exposed to nitrogen dioxide gas of 500 ppm.

From the above results described with reference to FIGS. 6A and 6B to 9A and 9B and FIG. 10, one can see that if silver nano wires are on a tungsten disulfide layer, it is possible to significantly improve performance of a gas sensor.

The above result may result from an n-type doping of a p-type tungsten disulfide layer, when may occur when the silver nano wires are formed on the tungsten disulfide layer. To verify a change in doping state of the tungsten disulfide layer caused by the presence of the silver nano material, a plurality of silver nano clusters having different amounts of silver were deposited on a tungsten disulfide layer using a thermal evaporator, and were measured using an ultraviolet photoelectron spectroscopy (UPS). The results of the UPS measurement will be described with reference to FIGS. 11 through 14.

Figure 11:
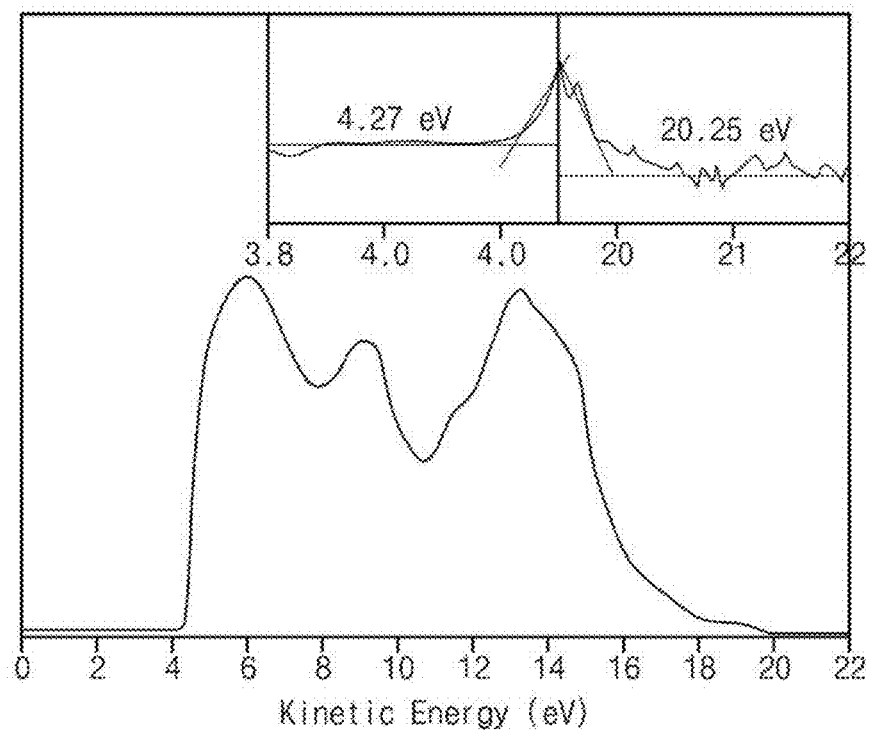
FIGS. 11 through 13 are ultraviolet photoelectron spectroscopy (UPS) graphs, which were measured by changing an amount of silver nano cluster provided on a tungsten disulfide layer formed by the method according to example embodiments of the inventive concept.
Figure 12:
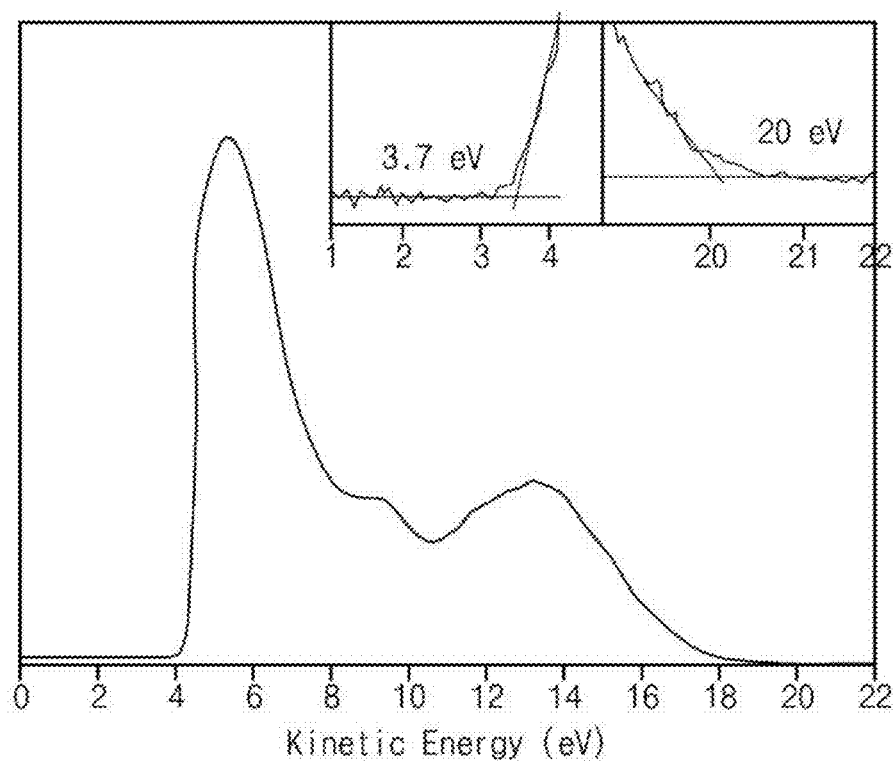
Figure 13:
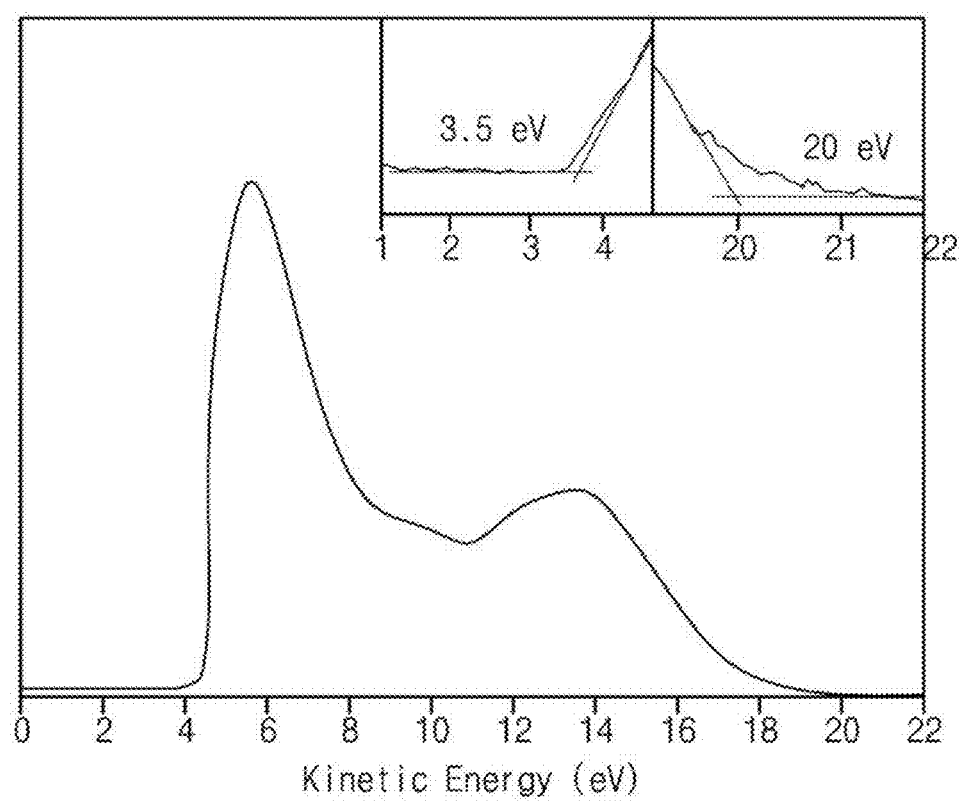

FIGS. 11 through 13 are UPS graphs, which were measured by changing an amount of silver nano cluster provided on a tungsten disulfide layer formed by the method according to example embodiments of the inventive concept.

In detail, FIGS. 11 through 13 are UPS graphs, which were respectively obtained from a tungsten disulfide layer without silver nano cluster, a tungsten disulfide layer provided with a plurality of silver nano clusters having a diameter of 0.3 nm, a tungsten disulfide layer provided with a plurality of silver nano clusters having a diameter of 0.6 nm. From the results of the UPS measurement, the inventor found that the tungsten disulfide layer without silver nano cluster had a work function of 5.22 eV, the tungsten disulfide layer provided with the silver nano clusters having the diameter of 0.3 nm had a work function of 4.9 eV, and the tungsten disulfide layer provided with the silver nano clusters having the diameter of 0.6 nm had a work function of 4.7 eV.

Figure 14:
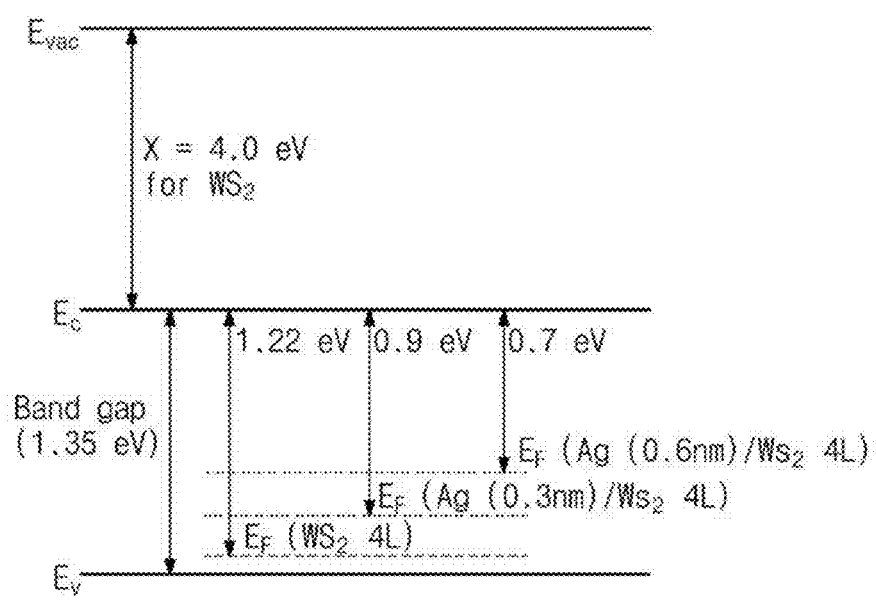
FIG. 14 is an energy band diagram showing Fermi energy levels calculated on the basis of UPS results of FIGS. 11 through 13.

FIG. 14 is an energy band diagram showing Fermi energy levels calculated on the basis of UPS results of FIGS. 11 through 13.

As shown in FIG. 14, an increase in diameter of the silver nano cluster and the consequent increase in amount of silver leads to an n-type doping of the p-type tungsten disulfide layer, and this may allow the tungsten disulfide layer to have an energy band structure similar to that of an intrinsic semiconductor. In other words, in the case where a silver nano material is formed on a tungsten disulfide layer, the tungsten disulfide layer can have a higher Fermi level, and this makes it possible to improve performance of a gas sensor including a tungsten disulfide layer with a silver nano material.

So far, gas sensors with high sensitivity and methods of manufacturing the same have been described. According to example embodiments of the inventive concept, it is possible to manufacture a gas sensor, in which a transition metal chalcogenide layer is provided to have a uniform thickness and a large area, and by forming a metal nano material on the transition metal chalcogenide layer, it is possible to improve sensitivity and gas adsorption efficiency of the gas sensor.

While example embodiments of the inventive concepts have been particularly shown and described, it will be understood by one of ordinary skill in the art that variations in form and detail may be made therein without departing from the spirit and scope of the attached claims.

EXPLANATION OF THE SIGNS

1000: substrate
1200: transition metal chalcogenide layer
1400: metal nano material
1600: electrode

The invention claimed is:

1. A method of manufacturing a gas sensor, comprising:
   forming a transition metal chalcogenide layer on a substrate; and
   forming an electrode on the transition metal chalcogenide layer,
   wherein the transition metal chalcogenide layer comprises a gas sensing region of the gas sensor,
   wherein the forming of the transition metal chalcogenide layer comprises:
      forming a transition metal oxide layer on the substrate using an atomic layer deposition process; and
      chalcogenizing the transition metal oxide layer,
   wherein the chalcogenizing of the transition metal oxide layer comprises:
      heating the transition metal oxide layer while supplying hydrogen sulfide on the transition metal oxide layer, wherein the heating of the transition metal oxide layer comprises:
  performing a first thermal treatment at a first temperature, while supplying hydrogen on the substrate; and
  performing a second thermal treatment at a second temperature higher than the first temperature, while supplying the hydrogen sulfide on the substrate.

2. The method of claim 1, further comprising forming a metal nano material on the transition metal chalcogenide layer.

3. The method of claim 2, wherein the forming of the metal nano material comprises:
  applying liquid comprising a metal nano material on the transition metal chalcogenide layer; and
  heating the substrate in an inert gas atmosphere to evaporate the liquid.

4. The method of claim 1, wherein the transition metal oxide layer comprises tungsten oxide; and
  the transition metal chalcogenide layer comprises tungsten disulfide.

5. The method of claim 4, further comprising forming a metal nano material on the transition metal chalcogenide layer.

6. The method of manufacturing a gas sensor, comprising:
  forming a transition metal chalcogenide layer on a substrate; and
  forming an electrode on the transition metal chalcogenide layer,
  wherein the forming of the transition metal chalcogenide layer comprises:
  forming a tungsten oxide layer on the substrate using an atomic layer deposition process; and
  heating the tungsten oxide layer while supplying hydrogen sulfide on the tungsten oxide layer, to form a tungsten disulfide layer,
  wherein the beating of the tungsten oxide layer comprises:
    performing a first thermal treatment at a first temperature, while supplying hydrogen on the substrate: and
    performing a second thermal treatment at a second temperature higher than the first temperature, while supplying the hydrogen sulfide on the substrate.

7. The method of claim 6, wherein the first thermal treatment comprises thermally treating the substrate at a temperature of 300° C. to 500° C. for 30 to 60 minutes, during the supplying of the hydrogen on the substrate, and
  the second thermal treatment comprises thermally treating the substrate at a temperature of 700° C. to 1000° C. for 30 to 60 minutes, during the supplying of the hydrogen sulfide on the substrate.

8. The method of claim 7, further comprising forming a metal nano material on the transition metal chalcogenide layer.

9. A method of manufacturing a gas sensor, comprising:
  forming a transition metal chalcogenide layer on a substrate;
  forming a band gap control layer on the transition metal chalcogenide layer to control a band gap of the transition metal chalcogenide layer; and
  forming an electrode on the transition metal chalcogenide layer,
  wherein the transition metal chalcogenide layer comprises a gas sensing region of the gas sensor,
  wherein the forming of the transition metal chalcogenide layer comprises:
    forming a transition metal oxide layer on the substrate using an atomic layer deposition process; and
    heating the transition metal oxide layer while supplying hydrogen sulfide on the transition metal oxide layer,
  wherein the heating of the transition metal oxide layer comprises:
    performing a first thermal treatment at a first temperature, while supplying hydrogen on the substrate; and
    performing a second thermal treatment at a second temperature higher than the first temperature, while supplying the hydrogen sulfide on the substrate.

10. The method of claim 9, wherein the forming of the band gap control layer comprises forming a metal nano material on the transition metal chalcogenide layer.

11. The method of claim 10, wherein the metal nano material comprises at least one selected from Ag, Pt, Au and Pd.

12. A method of forming a transition metal chalcogenide layer, comprising:
  depositing a transition metal oxide layer on a substrate using an atomic layer deposition process; and
  chalcogenizing the transition metal oxide layer to synthesize the transition metal chalcogen layer
  wherein the transition metal chalcogenide layer comprises a gas sensing region,
  wherein the chalcogenizing of the transition metal oxide layer comprises:
    performing a first thermal treatment at a first temperature, while supplying hydrogen on the substrate; and
    performing a second thermal treatment at a second temperature higher than the first temperature, while supplying a hydrogen sulfide on the substrate.

13. The method of claim 12, further comprising forming a metal nano material on the transition metal chalcogenide layer.

* * * * *